US011472927B2

(12) United States Patent
Andrianov et al.

(10) Patent No.: US 11,472,927 B2
(45) Date of Patent: Oct. 18, 2022

(54) POLYPHOSPHAZENES, METHODS OF MAKING, AND USES THEREOF

(71) Applicant: University of Maryland, College Park, College Park, MD (US)

(72) Inventors: Alexander K. Andrianov, Gaithersburg, MD (US); Alexander Marin, Rockville, MD (US); Thomas R. Fuerst, Gaithersburg, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 15/777,135

(22) PCT Filed: Nov. 18, 2016

(86) PCT No.: PCT/US2016/062846
§ 371 (c)(1),
(2) Date: May 17, 2018

(87) PCT Pub. No.: WO2017/087844
PCT Pub. Date: May 26, 2017

(65) Prior Publication Data
US 2018/0327550 A1  Nov. 15, 2018

Related U.S. Application Data

(60) Provisional application No. 62/256,988, filed on Nov. 18, 2015.

(51) Int. Cl.
*A61K 39/39* (2006.01)
*C08G 79/025* (2016.01)
*A61K 39/00* (2006.01)

(52) U.S. Cl.
CPC ............ *C08G 79/025* (2013.01); *A61K 39/39* (2013.01); *A61K 2039/55511* (2013.01)

(58) Field of Classification Search
CPC .............................. A61K 39/39; C08G 79/025
See application file for complete search history.

(56) References Cited

U.S. PATENT DOCUMENTS

| 4,477,656 | A | * | 10/1984 | Longo .................. C08G 79/025 528/482 |
| 5,053,451 | A | | 10/1991 | Allcock et al. |
| 5,464,932 | A | | 11/1995 | Allcock |
| 5,494,673 | A | | 2/1996 | Andrianov et al. |
| 5,529,777 | A | | 6/1996 | Andrianov et al. |
| 5,760,271 | A | * | 6/1998 | Andrianov ............ C07F 9/067 558/157 |
| 5,842,471 | A | * | 12/1998 | Andrianov ........... C08G 79/025 528/398 |
| 7,217,781 | B2 | * | 5/2007 | Andrianov ........... C08G 79/025 528/398 |
| 9,061,001 | B2 | * | 6/2015 | Van Drunen Littel-van den Hurk .................... A61K 39/099 |
| 2006/0193820 | A1 | | 8/2006 | Andrianov et al. |
| 2008/0166390 | A1 | | 7/2008 | Andrianov et al. |
| 2009/0117637 | A1 | * | 5/2009 | Grunze .................. A61L 27/34 435/180 |
| 2011/0100091 | A1 | | 5/2011 | Harrup |

FOREIGN PATENT DOCUMENTS

| WO | 1998039386 A1 | 9/1998 |
| WO | 1998058014 A1 | 12/1998 |
| WO | 2010043039 A1 | 4/2010 |

OTHER PUBLICATIONS

Andrianov et al., Polyphosphazene vaccine delivery vehicles: state of development and perspectives, Polyphosphazenes for biomedical applications, pp. 47-63. 2009.
Andrianov et al., Synthesis and biologically relevant properties of polyphosphazene polyacids, Biomacromolecules, vol. 5, No. 5, pp. 1999-2006. 2004.
Andrianov et al., Hydrolytic degradation of ionically cross-linked polyphosphazene microspheres, Journal of Applied Polymer Science, vol. 53, No. 12, pp. 1573-1578. 1994.
Payne et al., Poly[di(carboxylatophenoxy)phosphazene] (PCPP) is a potent immunoadjuvant for an influenza vaccine, Vaccine, vol. 16, No. 1, pp. 92-98. 1998.
Palmer et al., The effect of stable macromolecular complexes of ionic polyphosphazene on HIV Gag antigen and on activation of human dendritic cells and presentation to T-cells, Biomaterials, Jul. 11, 2014, vol. 35, No. 31, pp. 3876-3886.

* cited by examiner

*Primary Examiner* — Jared Barsky
(74) *Attorney, Agent, or Firm* — Hodgson Russ LLP

(57) ABSTRACT

Provided are polyphosphazenes and methods of making and using the polyphosphazenes. The polyphosphazenes can be essentially chloride free. The polyphosphazenes can be phosphazene polyacids. The polyphosphazenes can be used as surface coatings, or as adjuvants when combined with antigens.

13 Claims, 4 Drawing Sheets

POLYPHOSPHAZENES, METHODS OF MAKING, AND USES THEREOF

CROSS REFERENCE TO RELATED APPLICATIONS

This application claims priority to U.S. Provisional Application No. 62/256,988, filed on Nov. 18, 2015, the disclosure of which is hereby incorporated by reference.

FIELD OF THE DISCLOSURE

The disclosure generally relates to polyphosphazenes, methods of making polyphosphazenes, and uses of polyphosphazenes.

BACKGROUND OF THE DISCLOSURE

Immunoadjuvants show a great potential in the development of new generation vaccines. In particular, polyphosphazene adjuvants hold promise as vaccine adjuvants as they demonstrated a significant potential in various animal model, as well as in clinical trials. The advantage of polyphosphazene adjuvants is also in their synthetic origin and well defined structure. Further advantage of polyphosphazene adjuvants is that they are water-soluble under physiological conditions and thereby do not usually form bi-phasic systems, which allows formulating them with vaccine antigens in a single phase system, such as solution. However, polyphosphazene adjuvants can occasionally display phase separation or aggregation in the presence of an antigen or other components of the formulation, which is difficult to predict and can result in the highly undesirable decrease in the stability and shorter shelf life of the formulation, increased reactogenicity, and in the lower immune responses it elicits. There has been understanding that sodium salts or multivalent cations at certain concentrations can introduce instability, such as aggregation and generally phase separation, in solutions of polyphosphazene adjuvants, such as solutions of poly[di(carboxylatophenoxy)phosphazene], or PCPP (A. K. Andrianov, et al. Biomacromolecules 2004, 5, 5, 1999-2006). This undesirable phenomenon can be also amplified in the presence of vaccine antigen. Thereby an improved polyphosphazene adjuvant that affords a greater resistance to aggregation in the presence of destabilizing excipients, such as sodium salts, is needed for the development of stable vaccine formulations.

Polyphosphazene adjuvants typically contain chlorides as by-products of their synthesis. U.S. Pat. No. 5,053,451 to Allcock et al. describes preparation of PCPP, which uses hydrochloric acid for its isolation. This method inevitably leads to a contamination of the polyphosphazene product with chlorides, such as sodium or potassium chlorides. U.S. Pat. No. 5,842,471 to Andrianov et al. describes preparation of polyphosphazene adjuvant, which uses sodium chloride for the isolation of the polyphosphazene product. This method yields in a fast and effective isolation of the polymer, however it also results in the contamination of polyphosphazenes with substantial amounts of chloride salt, such as sodium chloride. These methods, which have been used in the prior art to prepare polyphosphazene adjuvants capable of inducing an immune response in a human or an animal when combined with an appropriate antigen, result in the production of polyphosphazene immunoadjuvants comprising chlorides as a major contaminant. However, there has been no connection established in the prior art indicating that the elimination of chloride from polyphosphazene can improve stability of formulations and their resistance to aggregation in the presence of sodium ions.

SUMMARY OF THE DISCLOSURE

The present disclosure provides a polyphosphazenes that can be used as essentially chloride free adjuvants that can be used to generate formulations with improved stability against aggregation. It is further directed to methods of producing an essentially chloride free polyphosphazene adjuvant, which and is capable of forming formulations with improved stability against aggregation.

In an aspect, the present disclosure is directed to a preparation of polyphosphazenes polyacids, which can be useful as immunoadjuvants, microencapsulating agents, or microfabrication materials for microneedles. More particularly, this disclosure relates to the preparation of polyphosphazene polyacids from polyhalophosphazenes by reacting a polyhalophosphazene with functionalized metal alkoxides or aryloxides to effect macromolecular substitution of the polyhalophosphazene. In the present disclosure, the functionalized metal alkoxide or aryloxide is contained in a heterogeneous suspension of an alkyl ester of carboxylic acid in organic solvent.

In an aspect, the present disclosure is directed to a polyphosphazene adjuvant, which, when combined with the antigen, is capable of eliciting an immune response, in a human or in an animal, against the antigen.

In an aspect, the present disclosure is directed to a polyphosphazene adjuvant, which is essentially chloride free, and is capable of forming formulations with improved stability against aggregation. It is further directed to methods of producing an essentially chloride free polyphosphazene adjuvant, which and is capable of forming formulations with improved stability against aggregation.

In an aspect, a polyphosphazene adjuvant is disclosed, which, when combined with an antigen, elicits an immune response, in a human or in an animal, against such antigen, wherein polyphosphazene adjuvant is essentially chloride free and displays improved stability and greater resistance to aggregation. The polyphosphazene adjuvant further includes a readily soluble sodium salt of polyphosphazene adjuvant, which is essentially free of sodium chloride. The polyphosphazene adjuvant is further disclosed, which contains a low molecular weight sodium salt. However, such polyphosphazene adjuvant, contrary to the expectations based on the findings of the prior art for sodium salts, is not susceptible to a phase separation or aggregation in solution in the presence of destabilizing ions, such as sodium ions. It also describes the methods to prepare such essentially chloride free polyphosphazene adjuvants.

In an aspect, the present disclosure provides polyphosphazenes. The polyphosphazenes can be chloride-free polyphosphazenes. The polyphosphazenes can be polyphosphazene polyacids. Also, provided are compositions comprising one or more polyphosphazenes of the present disclosure. In accordance with one embodiment of the disclosure there is provided a product comprising an antigen and a polyphosphazene polyelectrolyte adjuvant, in which said polyphosphazene polyelectrolyte adjuvant is essentially chloride free with improved stability against aggregation, and the product elicits an immune response in the human or in the animal, against the antigen.

In an aspect, the present disclosure provides methods of making polyphosphazenes of the present disclosure. The methods can be based on pH induced phase separation of a chloride-free polyphosphazene. The methods can also be based on use of a modifying agent without using the protic analog of the modifying agent (e.g., the modifying agent is not co-melted with the protic analog of the modifying agent). Chloride free polyphosphazene adjuvants disclosed herein are prepared by inducing phase separation in polymer solution by varying the pH or ionic environment of the solution.

In an aspect, the present disclosure provides uses of polyphosphazenes of the present disclosure. For example, polyphosphazenes of the present disclosure can be used as immunoadjuvants. In various other example, polyphosphazenes of the present disclosure can be used as coatings (e.g., surface coatings).

In various examples, a method of forming a surface coating uses one or more polyphosphazenes of the present disclosure. In various examples, a surface coating comprises one or more polyphosphazenes of the present disclosure. In various examples, a surface coating is biocompatible, bactericidal, superhydrophobic, or a combination thereof.

Polyphosphazene polyacids of the present disclosure can be useful as immunoadjuvants. Immunoadjuvants show a great potential in the development of new generation vaccines. In particular, polyphosphazene adjuvants hold promise as vaccine adjuvants as they demonstrated a significant potential in various animal model, as well as in clinical trials. The advantage of polyphosphazene adjuvants is also in their synthetic origin and well defined structure. Further advantage of polyphosphazene adjuvants is that they are water-soluble under physiological conditions and thereby do not usually form bi-phasic systems, which allows formulating them with vaccine antigens in a single phase system, such as solution.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
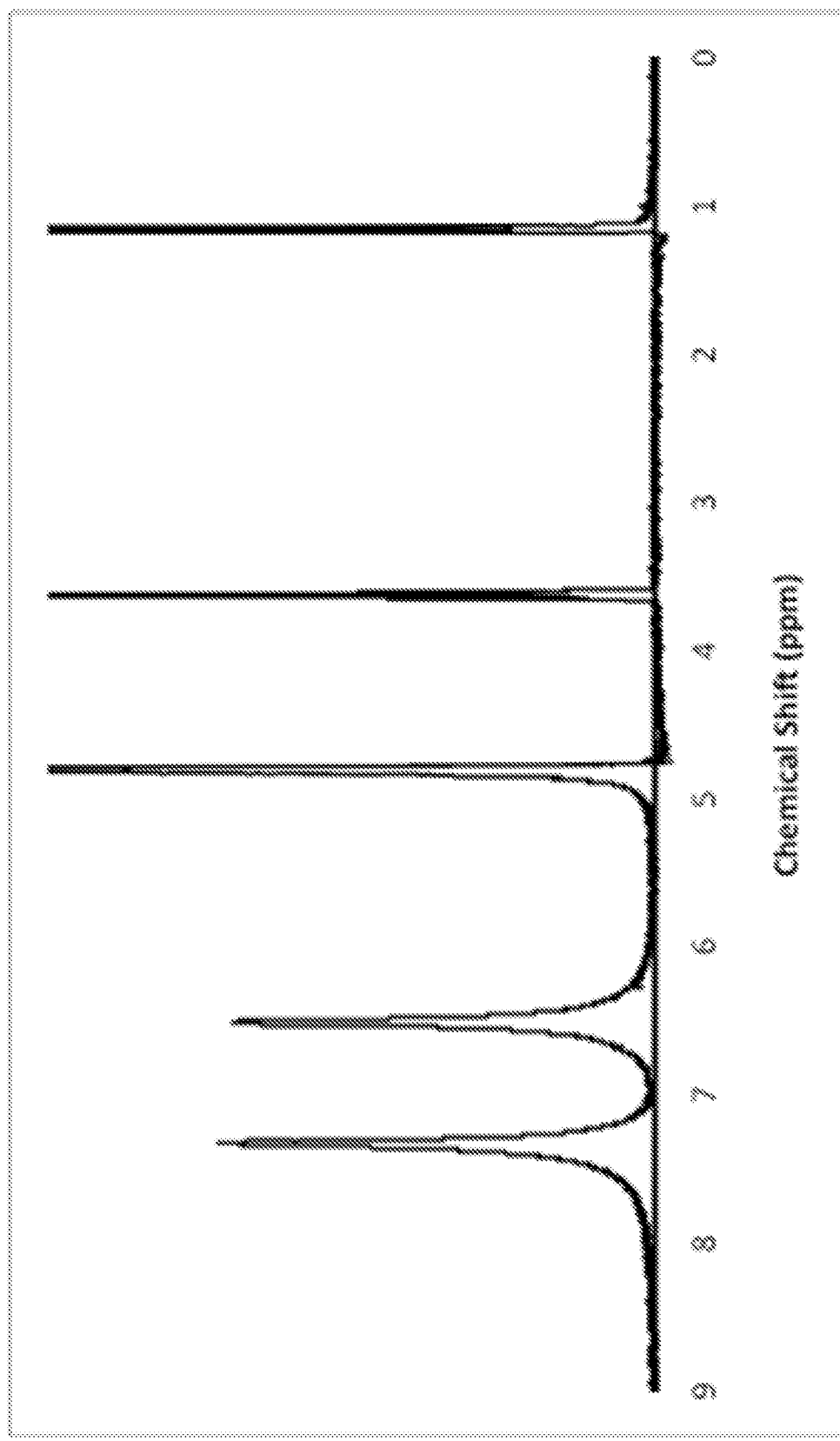
FIG. 1 shows an $^1$H-NMR spectrum of PCPP-HM in $D_2O$.

Although claimed subject matter will be described in terms of certain embodiments and examples, other embodiments and examples, including embodiments and examples that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides polyphosphazenes that can be used as essentially chloride free adjuvants that can be used to generate formulations with improved stability against aggregation. It is further directed to methods of producing an essentially chloride free polyphosphazene adjuvant, which and is capable of forming formulations with improved stability against aggregation. The polyphosphazenes are useful as adjuvants when combined with, or co-administered with, an antigen to which stimulation of an immune response is desired.

As used herein, unless otherwise stated, the term "group" refers to a chemical entity that has one terminus that can be covalently bonded to other chemical species. Examples of moieties include, but are not limited to:

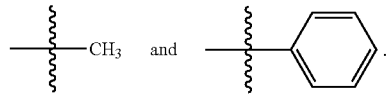

As used herein, unless otherwise stated, the term "moiety" refers to a chemical entity that has two or more termini that can be covalently bonded to other chemical species. Examples of moieties include, but are not limited to:

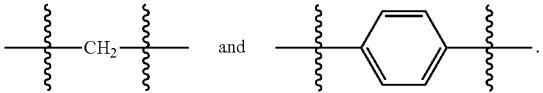

As used herein, unless otherwise indicated, the term "alkaryl" refers to an alkyl-substituted aryl group. A non-limiting example of an alkaryl is an ethylphenyl group.

As used herein, unless otherwise indicated, the term "aralkyl" refers to any group derived from an alkyl group by replacing one or more hydrogen atoms on the alkyl group with one or more aryl groups.

As used herein, unless otherwise indicated, the term "halogen" refers to fluorine atom, chlorine atom, bromine, or iodine atom, and the term "halo" means fluoro group (—F), chloro group (—Cl), bromo group (—Br), and iodo group (—I).

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_{12}$, including all integer numbers of carbons and ranges of numbers of carbons therebetween, alkyl group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, and alkynl groups), aryl groups, alkoxide groups, carboxylate groups, carboxylic acids, ether groups, and the like, and combinations thereof.

As used herein, unless otherwise indicated, the term "heteroalkyl" refers to branched or unbranched saturated hydrocarbon groups comprising at least one heteroatom. Examples of suitable heteroatoms include, but are not limited to, nitrogen, oxygen, sulfur, phosphorus, and halogens. The heteroalkyl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof.

As used herein, unless otherwise indicated, the term "alkylamine" refers to branched or unbranched saturated hydrocarbon groups comprising the following structures:

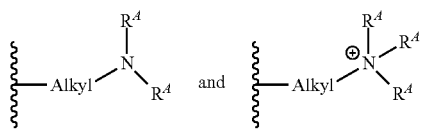

where $R^A$ is hydrogen and where Alkyl is as defined herein.

As used herein, unless otherwise indicated, "aminoalkyl" refers to a

group where each $R^b$ is selected independently from the group consisting of hydrogen atom, substituted or unsubstituted $C_1$ to $C_{12}$, including all integer numbers of carbons and ranges of numbers of carbons therebetween, alkyl chain substituted or unsubstituted phenyl, substituted or unsubstituted heteroaryl, substituted carbonyl, substituted sulfonyl, haloalkyl, and substituted or unsubstituted benzyl groups.

As used herein, unless otherwise indicated, "thioalkyl" refers to a

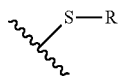

group, where R is selected from a substituted or unsubstituted $C_1$ to $C_{12}$, including all integer numbers of carbons and ranges of numbers of carbons therebetween, alkyl chain substituted or unsubstituted phenyl, substituted or unsubstituted heteroaryl, substituted carbonyl, substituted sulfonyl, haloalkyl, and substituted or unsubstituted benzyl groups.

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic group can be a $C_1$ to $C_{12}$, including all integer numbers of carbons and ranges of numbers of carbons therebetween, aliphatic group. The aliphatic group can be unsubstituted or substituted with one or more substituent. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, and the like, and combinations thereof.

As used herein, unless otherwise indicated, the term "oxyaliphatic" refers to branched or unbranched hydrocarbon groups containing an oxygen atom and, optionally, degrees of unsaturation. Degrees of unsaturation include, but are not limited to, alkenyl groups/moieties, alkynyl groups/moieties, or cyclic aliphatic groups/moieties. For example, the oxyaliphatic group can be a $C_1$ to $C_{12}$, including all integer numbers of carbons and ranges of numbers of carbons there between, oxyaliphatic group. The oxyaliphatic group can be unsubstituted or substituted with one or more substituents. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, and the like, and combinations thereof. Examples of oxyaliphatic groups include, but are not limited to, oxyalkyl and oxy(aliphatic) hydroxy (e.g., oxy(alkyl)hydroxy). Additional examples of oxyaliphatic groups include, but are not limited to, oxyfluoroalkyl groups (e.g., oxytrifluoroethyl groups).

As used herein, unless otherwise indicated, the term "thioaliphatic" refers to branched or unbranched hydrocarbon groups comprising a sulfur atom and, optionally, one or more degrees of unsaturation. Degrees of unsaturation include, but are not limited to, alkenyl groups/moieties, alkynyl groups/moieties, and cyclic aliphatic groups/moieties. For example, the thioaliphatic group can be a $C_1$ to $C_{12}$, including all integer numbers of carbons and ranges of numbers of carbons there between, thioaliphatic group. The thioaliphatic group can be unsubstituted or substituted with one or more substituent. Examples of substituents include, but are not limited to, various substituents such as, for example, halogens (—F, —Cl, —Br, and —I), additional aliphatic groups (e.g., alkenyl groups and alkynyl groups), aryl groups, alkoxides, carboxylates, carboxylic acids, ether groups, and the like, and combinations thereof. Examples of thioaliphatic groups include, but are not limited to, thioalkyl, thioalkaryl, and thioaralkyl.

As used herein, unless otherwise indicated, the term "aryl" refers to $C_5$ to $C_{14}$, including all integer numbers of carbons and ranges of numbers of carbons therebetween, aromatic or partially aromatic carbocyclic groups. The aryl group can comprise polyaryl moieties such as, for example, fused rings or biaryl moieties. The aryl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl groups include, but are not limited to, phenyl groups, biaryl groups (e.g., biphenyl groups), and fused ring groups (e.g., naphthyl groups).

As used herein, unless otherwise indicated, the term "oxyaryl" refers to groups comprising the following structure:

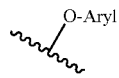

groups, where Aryl is as defined herein. Examples of oxyaryl groups include, but are not limited to, oxyphenyl groups and oxyphenylhydroxyl.

As used herein, unless otherwise indicated, the term "thioaryl" refers to groups comprising the following structure:

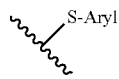

groups, where Aryl is as defined herein.

As used herein, unless otherwise indicated, the term "aminoaryl" refers to

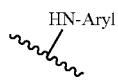

groups, where Aryl is as defined herein. The aminoaryl group can be substituted or unsubstituted with one or more substituent. Examples of substituents include, but are not limited to, various substituents such as, for example, aliphatic groups (e.g., alkenyl groups and alkynyl groups), aryl groups, alkoxides, carboxylates, carboxylic acids, ether groups, and the like, and combinations thereof.

As used herein, unless otherwise indicated, the term "arylamine" refers to groups comprising the following structures:

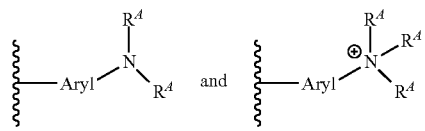

groups, where $R^A$ is hydrogen and where Aryl is as defined herein.

As used herein, unless otherwise indicated, the term "alkylarylamine" refers to groups comprising the following structures:

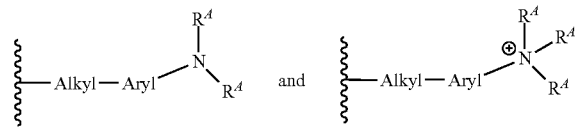

groups, where $R^A$ is hydrogen and where Alkyl and Aryl are as defined herein.

As used herein, unless otherwise indicated, the term "arylalkylamine" refers to groups comprising the following structures:

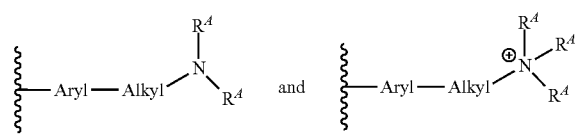

groups, where $R^A$ is hydrogen and where Alkyl and Aryl are as defined herein.

As used herein, unless otherwise indicated, the term "heteroaromatic" refers to a $C_5$ to $C_{14}$, including all integer numbers of carbons and ranges of numbers of carbons therebetween. monocyclic or bicyclic ring systems comprising one or two aromatic rings and containing at least one nitrogen, oxygen, or sulfur atom in an aromatic ring. The heteroaromatic groups can be substituted or unsubstituted. Examples of heteroaromatic groups include, but are not limited to, benzofuranyl, thienyl, furyl, pyridyl, pyrimidyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl groups.

As used herein, unless otherwise indicated, the term "carbohydrates" refers mono and poly hydroxyl ketone groups and aldehyde groups. Carbohydrates include, but are not limited to, monosaccharide groups, disaccharide groups, and polysaccharide groups. Examples of saccharide groups include, but are not limited to, glucose, mannose, galactose, other hexose groups/moieties and pentose groups/moieties, and combinations thereof.

Any salt described herein that does not expressly state that it includes chloride can be a chloride free salt.

In various embodiments the polyphospahzines are not subjected to post synthesis purification processes (e.g. to remove chloride ions) such as, for example, reprecipitation and/or ion exchange processes.

This disclosure is directed to a preparation of polyphosphazenes polyacids, which can be useful as immunoadjuvants, microencapsulating agents, or microfabrication materials for microneedles. More particularly, this disclosure relates to the preparation of polyphosphazene polyacids from polyhalophosphazenes by reacting a polyhalophosphazene with functionalized metal alkoxides or aryloxides to effect macromolecular substitution of the polyhalophosphazene. In the present disclosure, the functionalized metal alkoxide or aryloxide is contained in a heterogeneous suspension of an alkyl ester of carboxylic acid in organic solvent.

In an aspect, the present disclosure provides methods of making polyphosphazenes of the present disclosure. The methods can be based on pH induced phase separation of a chloride-free polyphosphazene. The methods of polyphosphazene preparation can also be based on use of a modifying agent as a solid, in a dispersion (suspension) form. This eliminates the use of protic analog of the modifying agent (e.g., the modifying agent is not co-melted with the protic analog of the modifying agent). Chloride free polyphosphazene adjuvants disclosed herein are prepared by inducing phase separation in polymer solution by varying the pH or ionic environment of the solution. This disclosure is more specifically directed to a polyphosphazene adjuvant, which, when combined with the antigen, is capable of eliciting an immune response, in a human or in an animal, against the antigen.

An embodiment is directed to a polyphosphazene adjuvant for use with a variety of antigens, wherein the polyphosphazene adjuvant is essentially chloride free, and is capable of forming formulations with improved stability against aggregation. It is further directed to methods of producing an essentially chloride free polyphosphazene adjuvant, which and is capable of forming formulations with improved stability against aggregation and is useful for use in combination with antigen administration.

A polyphosphazene adjuvant is disclosed, which, when combined with an antigen, elicits an immune response, in a human or in a non-human animal, against such antigen, wherein polyphosphazene adjuvant is essentially chloride free and displays improved stability and greater resistance to aggregation. The polyphosphazene adjuvant further includes a readily soluble sodium salt of polyphosphazene adjuvant, which is essentially free of sodium chloride. The polyphosphazene adjuvant is further disclosed, which contains a low molecular weight sodium salt. However, such polyphosphazene adjuvant, contrary to the expectations based on the findings of the prior art for sodium salts, is not susceptible to a phase separation or aggregation in solution in the presence of destabilizing ions, such as sodium ions. This disclosure also describes methods to prepare such essentially chloride free polyphosphazene adjuvants for use in combination with antigens.

In an aspect, the present disclosure provides polyphosphazenes (which are also referred to herein as polyorganophosphazenes). The polyphosphazenes can be chloride-free polyphosphazenes. The polyphosphazenes can be polyphosphazene polyacids. Also, provided are compositions comprising one or more polyphosphazenes of the present disclosure.

In accordance with one embodiment of the disclosure there is provided a product comprising an antigen and a polyphosphazene polyelectrolyte adjuvant, in which said polyphosphazene polyelectrolyte adjuvant is essentially chloride free with improved stability against aggregation, and the product elicits an immune response in the human or in the animal, against the antigen with which it is combined or co-administered.

A polyphosphazene adjuvant is disclosed, which, when combined with an antigen, elicits an immune response, in a human or in an animal, against such antigen, wherein polyphosphazene adjuvant is essentially chloride free and displays improved stability and greater resistance to aggregation. The polyphosphazene adjuvant further includes a readily soluble sodium salt of polyphosphazene adjuvant, which is essentially free of sodium chloride. The polyphosphazene adjuvant is further disclosed, which contains a low molecular weight sodium salt. However, such polyphosphazene adjuvant, contrary to the expectations based on the findings of the prior art for sodium salts, is not susceptible to a phase separation or aggregation in solution in the presence of destabilizing ions, such as sodium ions. It also describes the methods to prepare such essentially chloride free polyphosphazene adjuvants.

In one embodiment, the essentially chloride free polyphosphazene adjuvant comprises at least 85% (w/w) of polyphosphazene polymer, in the preferred embodiment, the essentially chloride free polyphosphazene adjuvant contains at least 90% of polyphosphazene polymer. The polyphosphazene polymer can be in its acidic or salt form. The preferred salt form is sodium, potassium or ammonium salt of the polyphosphazene. Polyphosphazene adjuvant can also contain residual water, low molecular weight salts, surfactants, degradation byproduct, residual organic solvents, reaction by-products, or any other materials.

In one embodiment the essentially chloride free polyphosphazene adjuvant contains less than 2% of chlorides. In another embodiment, the essentially chloride free polyphosphazene adjuvant contains less than 0.5% of chlorides. In yet another embodiment, the essentially chloride free polyphosphazene adjuvant contains less than 0.1% of chlorides. In the preferred embodiment, the essentially chloride free polyphosphazene adjuvant contains less than 0.1% of sodium chloride. The examples of chloride compounds are sodium chloride (NaCl), potassium chloride (KCl), potassium iodide (KI), lithium chloride (LiCl), copper (II) chloride ($CuCl_2$), silver chloride (AgCl) and organochlorides. In the most preferred embodiment, the essentially chloride free polyphosphazene adjuvant contains less than 0.1% of combined sodium chloride and potassium chloride.

In another embodiment, the essentially chloride free polyphosphazene adjuvant also contains sodium salts other than chlorides. The ability of sodium salt, such as sodium chloride, to phase separate polyphosphazene adjuvants more effectively than other salts, such as salts of lithium or potassium, has been described in the prior art. An essentially chloride free polyphosphazene adjuvant is disclosed, which contains sodium salts, wherein said essentially chloride free polyphosphazene adjuvant is combined with an antigen to elicit an immune response against such antigen and said formulations display high stability and minimal reactogenicity. Examples of such sodium salts include, but not limited to sodium phosphate, sodium sulfate, and sodium carbonate.

In yet another embodiment, the essentially chloride free polyphosphazene adjuvant also contains salts other than chlorides. Examples of such salts include phosphates, sulfates, nitrates, carbonates, borates, acetates, and citrates. The salt forming anion in such salts is preferably a divalent, trivalent, or a multivalent counterion. The examples of salt forming cations include ammonium, potassium, sodium, calcium, iron, magnesium, quaternary ammonium, spermine, and spermidine. Most preferably, essentially chloride free polyphosphazene adjuvant contains trisodium phosphate ($Na_3PO_4$, or sodium phosphate, tribasic), disodium hydrogen phosphate ($Na_2HPO_4$ or sodium phosphate, dibasic), sodium dihydrogen phosphate ($NaH_2PO_4$, or sodium phosphate, monobasic) or mixtures thereof.

The polyphosphazenes of the present disclosure, in a non-limiting embodiment, are polymers that may be biodegradable when administered to either humans or animals. Biodegradability of the polymer prevents eventual deposition and accumulation of polymer molecules at distant sites in the body, such as the spleen. The term biodegradable, as used herein, means a polymer that degrades within a period that is acceptable in the desired application, typically less than about five years and most preferably less than about one year.

The polyphosphazenes may be crosslinked ionically after being coated on an asperity, microprojection, or microneedle. Ionically crosslinkable polyphosphazenes, for example, can be crosslinked by treating a phosphazene polymer with a multivalent metal cation such as zinc, calcium, bismuth, barium, magnesium, aluminum, copper, cobalt, nickel, cadmium, or other multivalent metal cation known in the art; or with a multivalent organic cation such as spermine, spermidine, poly(ethyleneimine), poly(vinylamine), or other multivalent organic cation known in the art. Ionic crosslinking of the coating may be desired to improve the mechanical strength of the coating or to modulate the release of the at least one biologically active agent.

The formulation of the present disclosure comprises any liquid or solid that is compatible with the polyphosphazene of the present disclosure and the biologically active compound. It can be a solution or a dispersion, such as an emulsion or suspension. It can be water based or can contain organic solvents, or a mixture of water and organic solvents. In one embodiment, the formulation is a water or an aqueous based formulation. It can contain salts, acids, bases, or other excipients to maintain a desired pH and ionic strength. The formulation can be also a solid coating deposited on microneedles for intradermal delivery.

Polyphosphazenes are polymers with backbones consisting of alternating phosphorus and nitrogen atoms, separated by alternating single and double bonds. Each phosphorous atom is covalently bonded to two pendant groups ("R"). The repeat unit in polyphosphazenes has the following general formula:

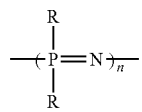

wherein n is an integer from 10 to 500,000, including all integer values and ranges therebetween. Each R may be the same or different.

In a non-limiting embodiment, the polyphosphazene has a single substituent and said polyphosphazene is a homopolymer. In yet another embodiment, the polyphosphazene has two or more types of pendant group and the groups vary randomly or regularly throughout the polymer. The phosphorus thus can be bound to two like groups, or to two different groups.

Polyphosphazene polyacids of the present disclosure, such as poly[di(carboxylatophenoxy)phosphazene] (PCPP), or poly[di(carboxylatoethylphenoxy)phosphazene] (PCEP) are especially useful as immunoadjuvants and as materials for microencapsulation, as described in U.S. Pat. No. 5,494,673, issued to Andrianov, et al.; and U.S. Pat. No. 5,529,777, issued to Andrianov, et al.

PCPP can be generally obtained by the macromolecular substitution of polydichlorophosphazene with sodium alkyl p-hydroxybenzoate in dioxane or tetrahydrofuran (THF) with subsequent hydrolysis of the ester group-containing polymer with base to yield PCPP as described in U.S. Pat. No. 5,053,451, issued to Allcock, et al. The modification reagent, sodium alkyl p-hydroxybenzoate, however, is not soluble in dioxane, tetrahydrofuran, diglyme, benzene, toluene or any other common solvent of choice for the modification reaction. To conduct the substitution reaction, this reagent can be obtained in situ by mixing, for example, ethyl hydroxybenzoate, with sodium spheres in dioxane and heating this mixture under reflux for 10 hours (U.S. Pat. No. 5,053,451) or by reacting propyl p-hydroxybenzoate, or propyl paraben, in THF with a 60% suspension of sodium hydride in mineral oil. The in situ synthesis of the reagent using reactive sodium, which is difficult to handle, increases process costs. The use of the less reactive suspension of sodium hydride in mineral oil can cause contamination of the resulting product causing undesirable side effects when used in vivo. Therefore it requires separation of oil from the contaminated product, resulting in extra process costs due to additional purification procedures and quality control.

Sodium propyl 4-hydroxybenzoate (sodium propyl paraben) is available commercially, but its use in the synthesis of PCPP requires sophisticated formulation efforts due to poor solubility of this reagent in the reaction mixture. In order to overcome this solubility limitation and avoid in process degradation of polyphosphazene due to insufficient amount of soluble reagent, the method utilizing sodium propyl 4-hydroxybenzoate was developed. This method introduced an additional step comprising dissolution of the salt in the reaction mixture by co-melting it with acidic propyl 4-hydroxybenzoate at elevated temperatures with stepwise addition of solvent, as described U.S. Pat. No. 5,760,271. Although the method eliminates challenges associated with the use of metal sodium, it also introduces an additional compound, propyl 4-hydroxybenzoate. Therefore it requires the use of supplementary manufacturing equipment, extends production time, and necessitates introduction of appropriate quality control methods for both, raw material and product, therefore resulting in increased production costs. Thereby, production processes are desired, which will provide for simplified manufacturing and quality control, fewer raw materials and reaction by-products, and lower costs. It has been also observed that the use of propyl 4-hydroxybenzoate can cause some polymer degradation and lead to undesirable losses in the molecular weight.

The experiment to synthesize PCPP was conducted, in which both propyl 4-hydroxybenzoate and co-melting procedure were inadvertently omitted. Despite the fact that the reaction mixture appeared heterogeneous with sodium propyl paraben forming a suspension, the reaction was allowed to proceed through the substitution and deprotection steps. Unexpectedly, the high molecular weight polymer was isolated as a product despite concerns about insufficient solution concentration of the reagent, incomplete substitution, and potential polymer degradation.

Polyphosphazene polyacids with higher molecular size are especially useful as they can potentially show superior immunoadjuvant activity and prolong shelf-life of the product through its longer degradation time. Thereby, the processes are needed that allow for the production of polyphosphazenes with higher molecular weight.

In an aspect, the present disclosure provides methods of making polyphosphazenes of the present disclosure. The methods can be based on pH induced phase separation of a chloride-free polyphosphazene. The methods can also be based on use of a modifying agent without using the protic analog of the modifying agent (e.g., the modifying agent is not co-melted with the protic analog of the modifying agent).

Chloride free polyphosphazene adjuvants disclosed herein are prepared by inducing phase separation in polymer solution by varying the pH or ionic environment of the solution.

In one embodiment, essentially chloride free polyphosphazene adjuvants disclosed herein are prepared by inducing phase separation in polymer solution by adding acid, which does not contain chloride anion. Examples of such acids include phosphoric, boric, carbonic, acetic, and oxalic acids. In the preferred embodiment, the acid is added to a polymer solution as a solution in water. In the most preferred embodiment, the acid is added at a concentration, which does not exceed 10% (w/v). Alternatively, phase separation can be induced by bubbling carbon dioxide gas through the solution of polymer until precipitation of the polymer is achieved. In the preferred embodiment, the acid is added in the amount sufficient to precipitate the polymer, but to maintain the pH of the resulting suspension above pH 3. In the most preferred embodiment, the acid is added in the amount sufficient to precipitate the polymer, but to achieve the pH of the resulting suspension between pH 5 and 6.5. The polyphosphazene adjuvant is then isolated from such suspension by filtration or centrifugation and dried to obtain the product in a solid form. Polyphosphazene adjuvant can then be dissolved in aqueous solutions. If needed, the appropriate amount of base, such as sodium hydroxide or potassium hydroxide, or salts, forming solutions with pH above pH 7 can be added to facilitate the dissolution and stored or used to prepare formulations with antigen. Alternatively, the solution of polyphosphazene adjuvant can then be dried by freeze drying or spray-drying, or other methods, to obtain polyphosphazene adjuvant in its readily soluble solid, granular, or powder form.

In another embodiment, essentially chloride free polyphosphazene adjuvants disclosed herein are prepared by inducing phase separation in polymer solution by adding salts of monovalent cations. The salts are selected to achieve the reduction in the pH of the solution or the dispersion of the polyphosphazene. In the preferred embodiment, the salt is added in the amount sufficient to precipitate the polymer, but to maintain the pH of the resulting suspension above pH 3. In the most preferred embodiment, the acid is added in the amount sufficient to precipitate the polymer, but to achieve the pH of the resulting suspension between pH 5 and 6.5. Examples of such salts include Potassium hydrogen phthalate, Disodium hydrogen phthalate, Dipotassium hydrogen phthalate, Sodium citrate, Sodium acetate, Sodium dihydrogen orthospate, Potassium dihydrogen orthophosphate, Disodium hydrogen orthophosphate. In the preferred embodiment, the salt is added to a polymer solution as a solution in water. In the most preferred embodiment, the acid is added at a concentration, which does not exceed 25% (w/v). Salts can be combined together or the pH of their solutions can be adjusted using acids or salts. In one embodiment, a buffer solution with pH 3.2 containing citric acid and trisodium citrate is used to precipitate polyphosphazene adjuvant. In another embodiment, a buffer solution with pH 4.4 containing Citric Acid and $Na_2HPO_4$, is used to precipitate polyphosphazene adjuvant. In yet another embodiment, a buffer solution with pH 6.0 containing $Na_2HPO_4$ and $NaH_2PO_4$, is used to precipitate polyphosphazene adjuvant. The polyphosphazene adjuvant is then isolated from such suspension by filtration or centrifugation and dried to obtain the product in a solid form. Alternatively, polyphosphazene adjuvant can be spray-dried. Polyphosphazene adjuvant can be also used without drying in a solution form.

In another embodiment, essentially chloride free polyphosphazene adjuvants disclosed herein are prepared by inducing phase separation in polymer solution by adding salts of divalent and multivalent cations. In one embodiment, the salt is added in the amount sufficient to precipitate the polymer, so that the pH of the resulting dispersion remains above pH 7.0. The examples of such salts include salts of calcium, magnesium, aluminum, spermine, spermidine, and ε-poly-L-lysine. In the preferred embodiment, such salts of multivalent cations include spermine tetrachloride or spermidine trihydrochloride. The pH of the dispersion can be lowered to facilitate phase separation or to improve the recovery of polyphosphazene adjuvant. The polyphosphazene adjuvant is then isolated from such suspension by filtration or centrifugation and dried to obtain the product in a solid form. Alternatively, polyphosphazene adjuvant can be spray-dried. Polyphosphazene adjuvant can be also used without drying as a dispersion or as a hydrogel. In one embodiment, polyphosphazene adjuvant is an aluminum salt of polyphosphazene adjuvant and is used as a dispersion or a hydrogel. In another embodiment, polyphosphazene adjuvant is an aluminum salt of poly[di(carboxylatophenoxy)phosphazene], or PCPP, adjuvant and is used as a dispersion or a hydrogel. In yet another embodiment, aluminum salt of PCPP comprises aluminum phosphate and is used as a dispersion or a hydrogel. If needed, polyphosphazene adjuvant can be then converted into a water-soluble form by using an appropriate chelator. For example, polyphosphazene adjuvant precipitated using calcium or magnesium salts can then be treated with a chelating agent, such as ethylenediaminetetraacetic acid (EDTA), or diethylene triamine pentaacetic acid (DTPA), or ethylene glycol tetraacetic acid (EGTA), or 1,2-bis(o-aminophenoxy)ethane-N,N,N',N'-tetraacetic acid (BAPTA), so that the precipitated polymer can be used in a water-soluble form.

In another embodiment, essentially chloride free polyphosphazene adjuvants disclosed herein are prepared by inducing phase separation in polymer solution by adding quaternary ammonium compounds, such as quaternary ammonium salts or hydroxides. The examples of such quaternary ammonium compounds include benzalkonium chloride, benzethonium chloride, methylbenzethonium chloride, cetalkonium chloride, cetylpyridinium chloride, cetrimonium, cetrimide, dofanium chloride, tetraethylammonium bromide, domiphen bromide, carnitine, cetyl trimethylammonium bromide (CTAB), stearalkonium chloride, cocamidopropyl betaine (CAPB), denatonium, dimethyldioctadecylammonium chloride, tetra-n-butylammonium bromide, tetramethylammonium chloride, tetramethylammonium hydroxide, and tetramethylammonium pentafluoroxenate. The polyphosphazene adjuvant is then isolated from such suspension by filtration or centrifugation and dried to obtain the product in a solid form.

If needed, the essentially chloride free polyphosphazene adjuvants disclosed herein can be further purified by methods commonly used for the purification of macromolecules, such as dialysis or column chromatography.

It is an object of the present disclosure to provide a process for producing polyorganophosphazene polyacids, such as PCPP, without the need for an additional excipient and process equipment for the preparation of the modifying reagent. It is also an object of the present disclosure to provide a process for producing polyorganophosphazene polyacids, such as PCPP, of higher molecular weight.

In accordance with an aspect of the present disclosure, there is provided a process for producing a polyorganophosphazene polyacid. The process comprises dispersing essentially insoluble sodium salt of alkyl ester of carboxylic acid in a solvent, contacting said solid dispersion with solution of polyhalophosphazene. Once the polymer is substituted, it can then be hydrolyzed to yield polyacid. Unexpectedly, it was also discovered that the production of polyphosphazene polyacids using said dispersion of essentially insoluble sodium salt of alkyl ester of carboxylic acid in a solvent results in polyphosphazene polyacids with molecular weights higher than those of polyphosphazenes produced using solubilized reagent.

In one embodiment, insoluble sodium salt of alkyl ester of carboxylic acid is dispersed in a solvent by mechanical means, such as stirring, vortexing, or by using ultrasonic baths or homogenizers. The insoluble sodium salt of alkyl ester of carboxylic acid can be dispersed at ambient or elevated temperatures, but preferably in the range between 4° C. and 180° C. The particle size is typically 1 micron or higher. Alternatively, the insoluble sodium salt of alkyl ester of carboxylic acid can be dispersed using supercritical fluids, such a supercritical carbon dioxide, which enables particle reduction to a range of 5-2000 nm.

The dispersion of sodium salt of alkyl ester of carboxylic acid in a solvent can be mixed with solution of polyhalophosphazene in the amounts sufficient to substitute halogen atoms of polyphosphazene. The order of addition can vary, but for the synthesis of copolymers, it is preferred that the sodium salt is added to the solution of polyhalophosphazene. The ester group can be then hydrolyzed, using basic reagents, such as potassium hydroxide, to yield carboxylic functions on the polymer.

In one embodiment, carboxylic acid of the present disclosure is hydroxybenzoic acid. In another embodiment, carboxylic acid is salicylic acid. In yet another embodiment, carboxylic acid is hydroxyphenylalkanoic acid, preferably, hydroxyphenylacetic acid.

In one embodiment, the alkyl ester of carboxylic acid has an alkyl moiety having from 1 to 6 carbon atoms. In another embodiment, the alkyl moiety is propyl.

In yet another embodiment, the metal salt of an alkyl ester of carboxylic acid is a Group I metal salt of an alkyl ester of carboxylic acid. In one embodiment, the Group I metal is sodium.

Polyhalophosphazenes which may be reacted include, but are not limited to, polychlorophosphazenes. In one embodiment, the polychlorophosphazene is polydichlorophosphazene. Other polyhalophosphazenes which may be employed include, but are not limited to, polyorganohalophosphazenes having organic side moieties, such as, for example poly[(carboxylatophenoxy)chlorophosphazene].

In one embodiment, the organic solvent in which the polyhalophosphazene is dissolved is diglyme. In another embodiment the organic solvent can be tetrahydrofuran, dioxane, or N-methylpyrrolidone. In another embodiment the organic solvent can be a mixture of solvents.

Polyorganophosphazenes which may be produced in accordance with the present disclosure include, but are not limited to, poly[di(carboxylatophenoxy)phosphazene], or PCPP, and poly[di(carboxylatoethylphenoxy)phosphazene] (PCEP).

In a non-limiting embodiment, the polymers of the present disclosure may be prepared by producing initially a reactive macromolecular precursor such as, but not limited to, poly(dichlorophosphazene). The pendant groups then are substituted onto the polymer backbone by reaction between the reactive chlorine atoms on the backbone and the appropriate organic nucleophiles, such as, for example, alcohols, amines, or thiols. Polyphosphazenes with two or more types of pendant groups can be produced by reacting a macromolecular precursor, such as poly(dichlorophosphazene) with two or more types of nucleophiles in a desired ratio. Nucleophiles can be added to the reaction mixture simultaneously or in sequential order. The resulting ratio of pendant groups in the polyphosphazene will be determined by a number of factors, including the ratio of starting materials used to produce the polymer, the order of addition, the temperature at which the nucleophilic substitution reaction is carried out, and the solvent system used. While it is difficult to determine the exact substitution pattern of the groups in the resulting polymer, the ratio of groups in the polymer can be determined easily by one skilled in the art.

In a non-limiting embodiment, the polyphosphazene polyelectrolytes, such as one containing carboxylic acid groups can be produced as follows. An organic compound containing hydroxyl group and ester group may be reacted with reactive chlorine atoms on the polymer backbone. One or a mixture of organic compounds can be used to result in a homopolymer or a copolymer having more than one type of pendant group. Hydroxyl groups of the organic compound can be activated with sodium, sodium hydride, or sodium hydroxide by procedures known in the art and then reacted with chlorine atoms attached to the polyphosphazene backbone. After the completion of the reaction, the ester functionalities of the pendant groups may be hydrolyzed to yield carboxylic acid functionalities. All ester functionalities can be hydrolyzed to achieve full conversion into the acid groups, or, if desired, the reaction can be stopped before completion, thereby resulting in a substituted copolymer containing both acid and ester functionalities. The polymer then can be dissolved in an aqueous solution at a desired concentration. The acid groups also can be converted into salt form, such as sodium or potassium, if required to improve solubility or to achieve desired polymer conformation and physico-chemical characteristics.

In an aspect, the present disclosure provides uses of polyphosphazenes of the present disclosure. For example, polyphosphazenes of the present disclosure can be used as immunoadjuvants. In various other example, polyphosphazenes of the present disclosure can be used as coatings (e.g., surface coatings).

In various examples, a method of forming a surface coating uses one or more polyphosphazenes of the present disclosure. In various examples, a surface coating comprises one or more polyphosphazenes of the present disclosure. In various examples, a surface coating is biocompatible, bactericidal, superhydrophobic, or a combination thereof.

Polyphosphazene polyacids of the present disclosure can be useful as immunoadjuvants. Immunoadjuvants show a great potential in the development of new generation vaccines. In particular, polyphosphazene adjuvants hold promise as vaccine adjuvants as they demonstrated a significant potential in various animal model, as well as in clinical trials. The advantage of polyphosphazene adjuvants is also in their synthetic origin and well defined structure. Further advantage of polyphosphazene adjuvants is that they are water-soluble under physiological conditions and thereby do not usually form bi-phasic systems, which allows formulating them with vaccine antigens in a single phase system, such as solution.

Polyphosphazene polyelectrolytes useful in the present disclosure are, in a non-limiting embodiment, polyphosphazenes containing acidic groups or salt thereof. Examples of such groups include -phenyl$CO_2H$, -phenyl$SO_3H$, -phenyl$PO_3H$, -(aliphatic)$CO_2H$, -(aliphatic)$SO_3H$, -(aliphatic)$PO_3H$, -phenyl(aliphatic)$CO_2H$, -phenyl(aliphatic)$SO_3H$, -phenyl(aliphatic)$PO_3H$, —$[(CH_2)_xO]_y$phenyl$CO_2H$, —$[(CH_2)_xO]_y$phenyl$SO_3H$, —$[(CH_2)_xO]_y$phenyl$PO_3H$, —$[(CH_2)_xO]_y$(aliphatic)$CO_2H$, —$[(CH_2)_xO]_y$(aliphatic)$SO_3H$, —$[(CH_2)_xO]_y$(aliphatic)$PO_3H$, —$[(CH_2)_xO]_y$phenyl(aliphatic)$CO_2H$, —$[(CH_2)_xO]_y$phenyl(aliphatic)$SO_3H$, —$[(CH_2)_xO]_y$phenyl(aliphatic)$PO_3H$, alkylamines, arylamines, alkylarylamines, arylalkylamines, $[(CH_2)_xO]_y$arylamines, $[(CH_2)_xO]_y$alkylarylamines, $[(CH_2)_xO]_y$arylalkylamines, where x is 1 to 8 and y is an integer of 1 to 20. The groups can be bonded to the phosphorous atom through, for example, an oxygen, sulfur, nitrogen, or carbon atom.

The polyphosphazenes of the present disclosure can be homopolymers, having one type of side groups, or mixed substituent copolymers, having two or more types of side groups. When polyphosphazene polymers of the present disclosure are copolymers and have two or more different types of side groups they can contain either different types of ionic groups or a combination of ionic and non-ionic groups. Side groups that do not contain ionic functionalities can be introduced in a polyphosphazene copolymer to modulate physical or physico-chemical properties of the polymer. Such side groups can be used, for example, to improve water solubility, to modulate biodegradability, to increase hydrophobicity, or to change chain flexibility of the polymer. These side groups (other than ionic groups as described above) may be one or more of a wide variety of substituent groups. As representative, non-limiting examples of such groups there may be mentioned: aliphatic; aryl; aralkyl; alkaryl; heteroaromatic; carbohydrates, including glucose, mannose; heteroalkyl; halogen; -oxyaryl including but not limited to -oxyphenyl, -oxyphenylhydroxyl; -oxyaliphatic including -oxyalkyl, and -oxy(aliphatic)hydroxyl, including oxy(alkyl)hydroxyl; -oxyalkaryl, -oxyaralkyl; -thioaryl; thioaliphatic including -thioalkyl; -thioalkaryl; thioaralkyl; aminoalkyl, aminoaryl, N-Ethylpyrrolidone, such as 2-(2-oxo-1-pyrrolidinyl)ethoxy; —NH—$[(CH_2)_x$—O—$]_y$-(aryl or aliphatic); and —O—$[(CH_2)_x$—O—$]_y$-(aryl or aliphatic); wherein x is 1-8 and y is an integer of 1 to 20.

In a non-limiting embodiment, the polymers of the present disclosure are homopolymers containing carboxylic acid side groups, such as poly[di(carboxylatophenoxy)phosphazene], or PCPP, and poly[di(carboxylatophenoxyethyl)phosphazene], and salts thereof, such as sodium or potassium salts, for example. In a preferred embodiment, the polymer of the present disclosure is a sodium salt of poly[di(carboxylatophenoxy)phosphazene]. In yet another embodiment, the polymer of the present disclosure is a potassium salt of poly[di(carboxylatophenoxy)phosphazene].

In a non-limiting embodiment, the polyphosphazene polymer has an overall molecular weight of 5,000 g/mol to 10,000,000 g/mol, and in another embodiment from 40,000 g/mol to 1,000,000 g/mol.

The polyphosphazenes of the present disclosure, in a non-limiting embodiment, are polymers that may be biodegradable when administered to either humans or animals. Biodegradability of the polymer prevents eventual deposition and accumulation of polymer molecules at distant sites in the body, such as the spleen. The term biodegradable, as used herein, means a polymer that degrades within a period that is acceptable in the desired application, typically less than about five years and most preferably less than about one year.

The polyphosphazenes may be crosslinked ionically to encapsulate vaccine antigens into micro- or nanospheres. Ionically crosslinkable polyphosphazenes, for example, can be crosslinked by treating a phosphazene polymer with a multivalent metal cation such as zinc, calcium, bismuth, barium, magnesium, aluminum, copper, cobalt, nickel, cadmium, or other multivalent metal cation known in the art; or with a multivalent organic cation such as spermine, spermidine, poly(ethyleneimine), poly(vinylamine), or other multivalent organic cation known in the art.

The formulation of polyphosphazene polyacids of the present disclosure with vaccine antigens can comprise any liquid or solid that is compatible with the polyphosphazene of the present disclosure and the biologically active compound. It can be a solution or a dispersion, such as an emulsion or suspension. It can be water based or can contain organic solvents, or a mixture of water and organic solvents. In one embodiment, the formulation is a water or an aqueous based formulation. It can contain salts, acids, bases, or other excipients to maintained a desired pH and ionic strength. The formulation can be also a solid coating deposited on microneedles for intradermal delivery or the entire material microneedles are made of.

Biologically active agents which are included in the formulation to provide an adjuvant effect comprise antigens, such as vaccine antigens. The vaccine antigens of the disclosure can be derived from a cell, a bacterium or virus particle or a portion thereof. The antigen can be a protein, peptide, polysaccharide, glycoprotein, glycolipid, or combination thereof which elicits an immunogenic response in a human; or in an animal, for example, a mammal, bird, or fish. The immunogenic response can be humoral, mucosal, or cell mediated.

Examples are viral proteins, such as influenza proteins, human immunodeficiency virus (HIV) proteins, Herpes virus proteins, and hepatitis A and B proteins. Additional examples include antigens derived from rotavirus, measles, mumps, rubella, and polio; or from bacterial proteins and lipopolysaccharides such as Gram-negative bacterial cell walls. Further antigens may also be those derived from organisms such as *Haemophilus* influenza, *Clostridium* antigens, including but not limited to, *Clostridium tetani*, *Corynebacterium diphtheria*, and *Nesisseria gonhorrhoae*, as well as anthrax antigens.

Antigenic or immunogenic agents that may be used in the immunogenic compositions of the disclosure include antigens from an animal, a plant, a bacteria, a protozoan, a parasite, a virus or a combination thereof. The antigenic or immunogenic agent may be any viral peptide, protein, polypeptide, virus-like particle (VLP) or a fragment thereof derived from a virus including, but not limited to, RSV-viral proteins, (RSV F glycoprotein, RSV G glycoprotein), influenza viral proteins (influenza virus neuramimidase, influenza virus hemagglutinin), herpes simplex viral protein, (herpes simplex virus glycoprotein including for example, gB, gC, gD, and gE). The antigenic or immunogenic agent for use in the compositions of the disclosure may be an antigen of a pathogenic virus such as, an antigen of adenovirdiae (mastadenovirus and aviadenovirus), herpesviridae (herpes simplex virus 1, herpes simplex virus 2, herpes simplex virus 5, and herpes simplex virus 6), leviviridae (levivirus, enterobacteria phase MS2, allolevirus), poxyiridae (chordopoxyirinae, parapoxvirus, avipoxvirus, capripoxvirus, leporipoxvirus, suipoxvirus, molluscipoxvirus, and entomopoxyirinae), papovaviridae (polyomavirus and papillomavirus), paramyxoviridae (paramyxovirus, parainfluenza virus 1, mobillivirus (measles virus), rubulavirus (mumps virus), pneumonovirinae (pneumovirus, human respiratory syncytial virus), metapneumovirus (avian pneumovirus and human metapneumovirus), picornaviridae (enterovirus, rhinovirus, hepatovirus (human hepatitis A virus), cardiovirus, and apthovirus), reoviridae (orthoreovirus, orbivirus, rotavirus, cypovirus, fijivirus, phytoreovirus, and oryzavirus), retroviridae (mammalian type B retroviruses, mammalian type C retroviruses, avian type C retroviruses, type D retrovirus group, BLV-HTLV retroviruses), lentivirus (human immunodeficiency virus 1 and human immunodeficiency virus 2), spumavirus, flaviviridae (hepatitis C virus), hepadnaviridae (hepatitis B virus), togaviridae (alphavirus (sindbis virus) and rubivirus (rubella virus), rhabdoviridae (vesiculovirus, lyssavirus, ephemerovirus, cytorhabdovirus, and necleorhabdovirus), arenaviridae (arenavirus, lymphocytic choriomeningitis virus, Ippy virus, and lassa virus), and coronaviridae (coronavirus and torovirus), caliciviridae (norovirus).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, *Capnocytophaga* polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

An antigenic agent can be a bacterial lipopolysaccharide (LPS) from gram-negative bacteria, such as *Neisseriae*, *Bordetellae*, *Branhamellas*, *Haemophilus* and *Moraxellae*, *Klebsiella*, *Pseudomonas*, *Burkolderia*, *Porphyromonas*, *Franciscella*, *Yersinia*, *Enterobacter*, *Salmonella*, *Shigella* or *E. coli*, and *N. meningitidis*. Antigenic agents can be derived from gram-positive bacteria, such as *Staphylococcus aureus* and *Streptococcus pneumonia*.

Examples of fungal antigens that may be immunogens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, Physaloptera polypeptides, Protostrongylus polypeptides, *Setaria* polypeptides, Spirocerca polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of immunogenic agents also include a DNA plasmid comprising a DNA sequence encoding an antigen to which an immune response is desired.

Alternatively, the antigenic or immunogenic agent in the immunogenic compositions of the disclosure may be a cancer or tumor antigen including but not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR (Epidermal growth factor receptor), HER2 antigen, polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, D.sub.156-22 found in colorectal cancer, TRA-1-85 (blood group H), C14 found in colonic adenocarcinoma, F3 found in lung adenocarcinoma, AH6 found in gastric cancer, Y hapten, Le.sup.y found in embryonal carcinoma cells, TL5 (blood group A), EGF receptor found in A431 cells, E.sub.1 series (blood group B) found in pancreatic cancer, FC 10.2 found in embryonal carcinoma cells, gastric adenocarcinoma antigen, CO-514 (blood group Lea) found in Adenocarcinoma, NS-10 found in adenocarcinomas, G49 found in EGF receptor of A431 cells, MH2 found in colonic adenocarcinoma, CA-19.9 found in colon cancer, gastric cancer mucins, $T_5A_7$ found in myeloid cells, $R_{24}$ found in melanoma, 4.2, $G_D3$, D1.1, OFA-1, GM2, OFA-2, $G_D2$, and M1:22:25:8 found in embryonal carcinoma cells, and SSEA-3 and SSEA-4 found in 4 to 8-cell stage embryos, and T cell receptor derived peptide from a Cutaneous T cell Lymphoma.

The polymer in combination with an antigen is used in an amount effective to provide the desired immune response. The immunogenic composition can be administered as a vaccine by any method known to those skilled in the art that elicits an immune response; including parenteral, transcutaneous, oral, or transmucosal administration. Preferably, the vaccine is administered parenterally (intravenously, intramuscularly, subcutaneously) or transcutaneously (intradermally). Non-limiting examples of routes of delivery to mucosal surfaces are intranasal (or generally, the nasal associated lymphoid tissue), oral, respiratory, vaginal and rectal.

In a non-limiting embodiment, the liquid formulation also may include vaccine adjuvants or immunostimulating compounds which, when the at least one biologically active agent is an antigen, enhance an immune response to the antigen in the recipient host. The liquid formulation may also include immune response modifying compounds, compounds that act through basic immune system mechanisms known as toll like receptors to induce selected cytokine biosynthesis. Typical examples of adjuvants and immune modulating compounds include, but are not limited to, aluminum hydroxide, aluminum phosphate, squalene, Freunds adjuvant, certain poly- or oligonucleotides (DNA sequences), such as CpG, Ribi adjuvant system, polyphosphazene adjuvants such as poly[di(carboxylatophenoxy) phosphazene] (PCPP) and poly[di(carboxylatoethylphenoxy) phosphazene] (PEPP), MF-59, saponins, such as saponins purified from the bark of the *Q. saponaria* tree, such as QS-21, derivatives of lipopolysaccharides, such as monophosphorlyl lipid (MPL), muramyl dipeptide (MDP) and threonyl muramyl dipeptide (tMDP); OM-174; nonionic block copolymers that form micelles such as CRL 1005; and Syntex Adjuvant Formulation. In case of polyphosphazene immunostimulating compounds, the compounds can act as both the adjuvants and the additives for the liquid formulation.

The liquid coating fluid formulation also may include one or more pharmaceutical acceptable and/or approved additives (excipients), antibiotics, preservatives, diluents and stabilizers. Such substances include but are not limited to water, saline, glycerol, ethanol, wetting or emulsifying compounds, pH buffering substances, stabilizing compounds such as polyols, for example trehalose, or the like.

In a non-limiting embodiment, the at least one biologically active agent may be formulated or encapsulated in various forms or encapsulation media, such as in microspheres, nanospheres, microcapsules, nanocapsules, microgels, nanogels, liposomes, or dendrimers. The above-mentioned forms may modulate the release profile in order to achieve a desirable biological (therapeutic) effect. For example, such forms may provide a controlled release of at least one biologically active agent over a desired period of time.

U.S. Pat. No. 5,494,673 discloses polyphosphazene polyelectrolytes that are useful as immunoadjuvants. The disclosures of U.S. Pat. No. 5,494,673 are hereby incorporated by reference in their entireties. The instant disclosure is also an improvement on the use of the polyphosphazene polyelectrolyte and antigen combinations disclosed in U.S. Pat. No. 5,494,673, and an improvement on the use of other polyphosphazene polyelectrolyte and antigen combinations disclosed elsewhere. The instant disclosure is also an improvement on the use of the polyphosphazene adjuvants disclosed in U.S. Patent Application Publication 20060193820 (filed Aug. 31, 2006). The disclosures of U.S. Patent Application Publication 20060193820 are hereby incorporated by reference in their entireties.

Polyacids can be used for preparation of superhydrophobic or superoleophobic surfaces or films. Superhydrophobic (water-repelling) surfaces comprise surfaces having a contact angle for water of greater than 150 degree and superoleophobic (oil repelling) surfaces comprise surfaces having a contact angle for an organic liquid of greater than 150 degree. Such coatings have multiple industrial applications, such as anti-sticking, anti-contamination, friction drag reduction, and self-cleaning coatings. In one embodiment such coatings can be created using fluorinated polyacids of the present disclosure. In the preferred embodiment, such coatings are formed using aqueous solution of poly[(carboxylatophenoxy)(trifluoroethoxy)phosphazene] of present disclosure via multilayer polyelectrolyte deposition process. Such fluorinated coatings can be also useful as biocompatible and bactericidal surfaces.

The steps of the method described in the various embodiments and examples disclosed herein are sufficient to carry out the methods of the present disclosure. Thus, in an embodiment, a method consists essentially of a combination of the steps of the methods disclosed herein. In another embodiment, a method consists of such steps.

In the following Statements, various examples of the methods and structures of the present disclosure described:

Statement 1. A polyphosphazene having the following structure:

(Structure I)

a salt thereof, or a crosslinked analog thereof, where R' and R" at each occurrence on the polyphosphazene are independently selected from aliphatic; aryl; aralkyl; alkaryl; heteroaromatic; carbohydrates; heteroalkyl; halogen; -oxyaryl; -oxyaliphatic; -oxyfluoroalkyl (e.g., oxytrifluoroethyl), -oxyalkaryl, -oxyaralkyl; -thioaryl; thioaliphatic; -thioalkaryl; thioaralkyl; aminoalkyl, aminoaryl, N-ethylpyrrolidone; —NH—[(CH$_2$)$_x$—O—]$_y$-(aryl or aliphatic); and —O—[(CH$_2$)$_x$—O—]$_y$-(aryl or aliphatic); where n is an integer from 10 to 500,000, x is an in integer from 1 to 8 and y is an integer from 1 to 5,000, including all integer values therebetween, (e.g., 1 to 20), and the polyphosphazene has less than 2% by weight chloride. In various examples, a polyphosphazene is soluble in aqueous media (e.g., water and buffered aqueous solutions (e.g., PBS, Tris, HEPES, etc.).

Statement 2. A polyphosphazene according to Statement 1, where R' and R" are at each occurrence on the polyphosphazene are independently selected from -phenylCO$_2$H, -phenylSO$_3$H, -phenylPO$_3$H, -(aliphatic)CO$_2$H, -(aliphatic)SO$_3$H, -(aliphatic)PO$_3$H, -phenyl(aliphatic)CO$_2$H, -phenyl(aliphatic)SO$_3$H, -phenyl(aliphatic)PO$_3$H, —[(CH$_2$)$_x$O]$_y$phenylCO$_2$H, —[(CH$_2$)$_x$O]$_y$phenylSO$_3$H, —[(CH$_2$)$_x$O]$_y$phenylPO$_3$H, —[(CH$_2$)$_x$O]$_y$(aliphatic)CO$_2$H, —[(CH$_2$)$_x$O]$_y$(aliphatic)SO$_{O3}$H, —[(CH$_2$)$_x$O]$_y$(aliphatic)PO$_3$H, —[(CH$_2$)$_x$O]$_y$phenyl(aliphatic)CO$_2$H, —[(CH$_2$)$_x$O]$_y$phenyl(aliphatic)SO$_3$H, - or [(CH$_2$)$_x$O]$_y$phenyl(aliphatic)PO$_3$H, where x is an in integer from 1 to 8 and y is an integer from 1 to 5,000, including all integer values therebetween (e.g., 1 to 20).

Statement 3. A polyphosphazene according to anyone of the preceding Statements, where 0 to 95%, including all 0.1% values and ranges therebetween, of R' and/or R" at each occurrence on the polyphosphazene are independently selected from aliphatic; aryl; aralkyl; alkaryl; heteroaromatic; carbohydrates; heteroalkyl; halogen; -oxyaryl; -oxyaliphatic; -oxyalkaryl, -oxyaralkyl; -thioaryl; thioaliphatic; -thioalkaryl; thioaralkyl; aminoalkyl, aminoaryl, N-ethylpyrrolidone; —NH—[(CH$_2$)$_x$—O—]$_y$-(aryl or aliphatic); and —O—[(CH$_2$)$_x$—O—]$_y$-(aryl or aliphatic), and where 5 to 100%, including all 0.1% values and ranges therebetween, of where R' and R" are at each occurrence on the polyphosphazene are independently selected from -phenylCO$_2$H, -phenylSO$_3$H, -phenylPO$_3$H, -(aliphatic)CO$_2$H, -(aliphatic)SO$_3$H, -(aliphatic)PO$_3$H, -phenyl(aliphatic)CO$_2$H, -phenyl(aliphatic)SO$_3$H, -phenyl(aliphatic)PO$_3$H, —[(CH$_2$)$_x$O]$_y$phenylCO$_2$H, —[(CH$_2$)$_x$O]$_y$phenylSO$_3$H, —[(CH$_2$)$_x$O]$_y$phenylPO$_3$H, —[(CH$_2$)$_x$O]$_y$(aliphatic)CO$_2$H, —[(CH$_2$)$_x$O]$_y$(aliphatic)SO$_3$H, —[(CH$_2$)$_x$O]$_y$(aliphatic)PO$_3$H, —[(CH$_2$)$_x$O]$_y$phenyl(aliphatic)CO$_2$H, —[(CH$_2$)$_x$O]$_y$phenyl(aliphatic)SO$_3$H, - or [(CH$_2$)$_x$O]$_y$phenyl(aliphatic)PO$_3$H, alkylamines, arylamines, alkylarylamines, arylalkylamines, [(CH$_2$)$_x$O]$_y$arylamines, [(CH$_2$)$_x$O]$_y$alkylarylamines, [(CH$_2$)$_x$O]$_y$arylalkylamines, where x is an in integer from 1 to 8 and y is an integer from 1 to 20.

Statement 4. A polyphosphazene according to any one of the preceding Statements, where R' and R" are carboxylatophenoxy groups (e.g., poly[di(carboxylatophenoxy)phosphazene]) or a combination of carboxylatophenoxy groups and trifluoroethoxy groups (e.g., poly[(carboxylatophenoxy)(trifluoroethoxy)phosphazene]).

Statement 5. A polyphosphazene according to any one of the preceding Statements, where the polyphosphazene is a salt and the cation is selected from ammonium, potassium, sodium, calcium, iron, magnesium, quaternary ammonium, spermine, spermidine, and combinations thereof.

Statement 6. A polyphosphazene according to any one of the preceding Statements, where the polyphosphazene is crosslinked covalently or noncovalently.

Statement 7. A composition comprising one or more polyphosphazenes (e.g., chlorine-free polyphosphazenes) of the present disclosure (e.g., one or more polyphosphazenes of Statements 1 to 6).

Statement 8. A composition according to Statement 7, where the composition further comprises one or more pharmaceutically acceptable carrier (e.g., one or more excipient).

Statement 9. A composition according to any one of Statements 7 or 8, where the composition further comprises one or more salts, where the one or more salts do not comprise a chloride ion.

Statement 10. A composition according to any one of Statements 7 to 9, where at least one of the one or more polyphosphazenes are crosslinked covalently or non-covalently.

Statement 11. A composition according to any one of Statements 7 to 10, where the composition further comprises an immunologically active compound and the immunologically active compound is encapsulated by the crosslinked polyphosphazene.

Statement 12. A method of making a polyphosphazene (e.g., a polyphosphazene of Statement 1) comprising: a) providing a reaction mixture comprising a polyphosphazene, b) adjusting the pH of the reaction mixture with a chloride-free acid such that a precipitate comprising the polyphosphazene is formed; and c) separating the precipitate from the reaction mixture to provide a polyphosphazene having a chloride content of less than 2% by weight (e.g., a polyphosphazene of Statement 1).

Statement 13. A method according to Statement 12, where the pH does not go below 3.0, but does not exceed 6.5.

Statement 14. A method according to any one of Statements 12 to 13, where the pH of the reaction mixture is adjusted by adding an acid salt comprising monovalent cations to the reaction mixture.

Statement 15. A method according to any one of Statements 13 or 14, where the acid salt is selected from the group potassium hydrogen phthalate, disodium hydrogen phthalate, dipotassium hydrogen phthalate, sodium citrate, sodium acetate, sodium dihydrogen orthophospate, potassium dihydrogen orthophosphate, or disodium hydrogen orthophosphate.

Statement 16. A method according to any one of Statements 12 or 13, where the pH of the reaction mixture is adjusted by addition of carbon dioxide to the reaction mixture.

Statement 17. A method according to any one of Statements 12 to 16, further comprising adding zinc, calcium, bismuth, barium, magnesium, aluminum, copper, cobalt, nickel, cadmium, or a combination thereof to the reaction mixture prior to adjustment of the pH, where the polyphosphazene is ionically crosslinked.

Statement 18. A method according to any one of Statements 12 to 16, further comprising adding of spermine, spermidine, poly(ethyleneimine), poly(vinylamine), or a combination thereof to the reaction mixture prior to adjustment of the pH, where the polyphosphazene is ionically crosslinked.

Statement 19. A method according to any one of Statements 12 to 18, where the polyphosphazene is poly[di(carboxylatophenoxy)phosphazene].

Statement 20. A polyphosphazene having the following structure:

(Structure II)

a salt thereof, or a crosslinked analog thereof, where R' and R" at each occurrence on the polyphosphazene are independently selected from -phenylCO$_2$H, -phenylSO$_3$H, -phenylPO$_3$H, -(aliphatic)CO$_2$H, -(aliphatic)SO$_3$H, -(aliphatic)PO$_3$H, -phenyl(aliphatic)CO$_2$H, -phenyl(aliphatic)SO$_{03}$H, -phenyl(aliphatic)PO$_3$H, —[(CH$_2$)$_x$O]$_y$phenylCO$_2$H, —[(CH$_2$)$_x$O]$_y$phenylSO$_3$H, —[(CH$_2$)$_x$O]$_y$phenylPO$_3$H, —[(CH$_2$)$_x$O]$_y$(aliphatic)CO$_2$H, —[(CH$_2$)$_x$O]$_y$(aliphatic)SO$_{03}$H, —[(CH$_2$)$_x$O]$_y$(aliphatic)PO$_3$H, -[(CH$_2$)$_x$O]$_y$phenyl(aliphatic)CO$_2$H, —[(CH$_2$)$_x$O]$_y$phenyl(aliphatic)SO$_3$H, - or [(CH$_2$)$_x$O]$_y$phenyl(aliphatic)PO$_3$H, alkylamines, arylamines, alkylarylamines, arylalkylamines, [(CH$_2$)$_x$O]$_y$arylamines, [(CH$_2$)$_x$O]$_y$alkylarylamines, [(CH$_2$)$_x$O]$_y$arylalkylamines, where x is 1 to 8 and y is an integer of 1 to 20, where n is an integer from 2,500 to 500,000, including all integer values and ranges therebetween, and the polyphosphazene has a z-average molecular diameter of at least 70 nm, at least 80 nm, at least 90 nm, or at least 100 nm when dissolved under physiological conditions (e.g., in phosphate buffered saline (PBS) at pH 7.4). In various examples, a polyphosphazene is soluble in aqueous media (e.g., water and buffered aqueous solutions (e.g., PBS, Tris, HEPES, etc.).

Statement 21. A polyphosphazene according to Statement 20, where the polyphosphazene has less than 2% by weight chloride.

Statement 22. A polyphosphazene according to any one of Statements 20 or 21, where R' and R" are carboxylatophenoxy groups (e.g., poly[di(carboxylatophenoxy)phosphazene]) or a combination of carboxylatophenoxy groups and trifluoroethoxy groups (e.g., poly[(carboxylatophenoxy)(trifluoroethoxy)phosphazene]).

Statement 23. A polyphosphazene according to any one of Statements 20 to 22, where the polyphosphazene is a salt and the cation is selected from ammonium, potassium, sodium, calcium, iron, magnesium, quaternary ammonium, spermine, spermidine, and combinations thereof.

Statement 24. A polyphosphazene according to any one of Statements 20 to 23, where the polyphosphazene is crosslinked covalently or noncovalently.

Statement 25. A composition comprising one or more polyphosphazene polyacids of the present disclosure (e.g., one or more polyphosphazenes of Statement 20).

Statement 26. A composition according to Statement 25, where the composition further comprises a pharmaceutically acceptable carrier (e.g., excipient).

Statement 27. A composition according to any one of Statements 25 or 26, where the composition further comprises one or more salts, where the one or more salts do not comprise a chloride ion.

Statement 28. A composition according to any one of Statements 25 to 27, where the polyphosphazene is crosslinked covalently or noncovalently.

Statement 29. A composition according to any one of Statements 25 to 28, where the composition further comprises an immunologically active compound and the immunologically active compound is encapsulated by the crosslinked polyphosphazene.

Statement 30. A method of making a polyphosphazene of the present disclosure (e.g., a polyphosphazene of Statements 1 to 6 or Statements 20 to 24) comprising: a) forming a reaction mixture (e.g., a heterogeneous reaction mixture) comprising a polyhalophosphazene and a sodium salt of an alkyl ester of a carboxylic acid in a solvent, where the sodium salt of an alkyl ester of a carboxylic acid in a solvent is present in the reaction mixture as a dispersion, where the polyphosphazene (e.g., a polyphosphazene of claim 1 or claim 20) is formed.

Statement 31. A method according to Statement 30, where the method further comprises forming a dispersion comprising the sodium salt of an alkyl ester of a carboxylic acid in a solvent and subsequently the dispersion comprising the sodium salt of an alkyl ester of a carboxylic acid in a solvent is combined with the polyhalophosphazene.

Statement 32. A method according to any one of Statements 30 or 31, where the sodium salt of an alkyl ester of a carboxylic acid is sodium propyl p-hydroxybenzoate.

Statement 33. A method according to any one of Statements 30 to 32, where the polyphosphazene has at least 60%, at least 65%, at least 70%, at least 75%, at least 80%, at least 85%, or at least 90% of the number of repeat units as the polyhalophosphazene.

Statement 34. A method of enhancing an immunological response to an immunologically active compound in an individual comprising administering one or more composition of the present disclosure comprising both a polyphosphazene of the present disclosure and an immunologically active compound (e.g., a composition of Statements 11 or 29) to the individual.

The following examples are presented to illustrate the present disclosure. They are not intended to limiting in any matter.

Example 1

This example provides a description of the synthesis of a PCPP of higher molecular weight (PCPP-HM) using solid dispersion of the modifying agent.

The reaction vessel was charged with 89.7 g (0.444 mol) of sodium salt of propyl 4-hydroxybenzoate (NaPP) under anhydrous nitrogen atmosphere. To this salt, 70 ml of anhydrous diglyme was added stepwise in 10 mL aliquots while stirring under a continuous nitrogen flow at ambient temperature. The resulting suspension was then stirred at 100-120° C. for 30 minutes and cooled to ambient temperature. The suspension was added to 30 mL of 0.40 M PDCP solution in diglyme upon stirring under a continuous nitrogen flow. The reaction mixture was then stirred for two hours at 100-120° C., cooled to 95° C., and 65 mL of 13 M aqueous potassium hydroxide was added to the flask at this temperature. After cooling down to ambient temperature, 200 mL of water was added to dissolve the polymer, and the mixture was transferred to a separation funnel. The aqueous phase was then collected and 200 mL of ethanol was added. The precipitate was allowed to settle, the supernatant decanted, and the precipitate was dissolved in deionized water to make a total volume of 200 mL.

The resulting solution was then precipitated with the addition of 100 mL 15% (w/v) aqueous sodium chloride, the precipitate collected, and the procedure was repeated. Finally, the polymer was dissolved in water to a volume of 150 mL, precipitated with the addition of ethanol, and dried under vacuum. The yield was 2.6 g (60%).

Figure 2:
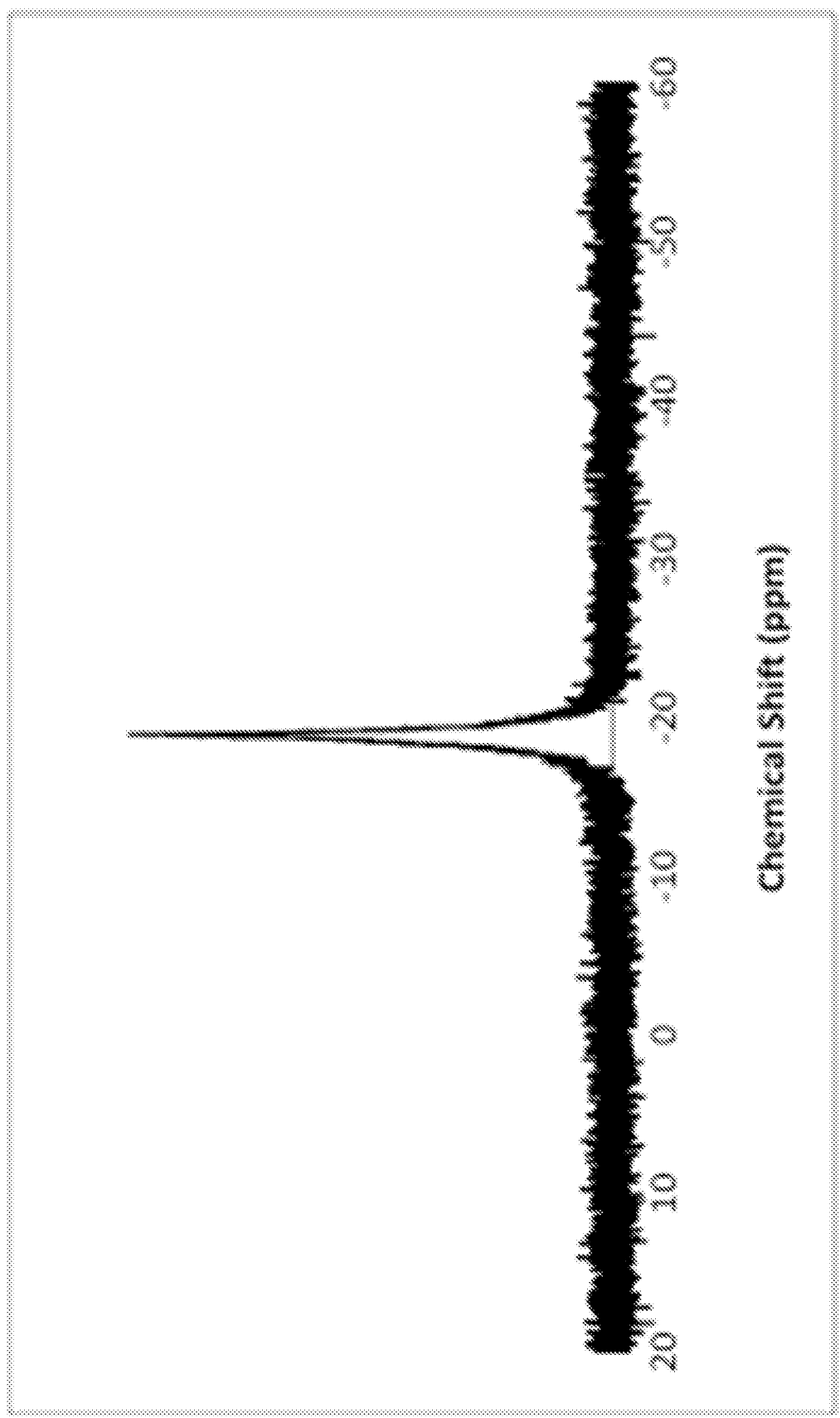
FIG. 2 shows $^{31}$P-NMR spectrum of PCPP-HM in $D_2O$.

$^1$H-NMR and $^{31}$P-NMR were performed in $D_2O$ using a Bruker Ascend 400. $^1$H-NMR showed two singlet peaks at 7.3 ppm and 6.5 ppm corresponding to the aromatic protons on the side group (FIG. 1). $^{31}$P-NMR showed one single peak at −18.9 ppm indicating complete substitution FIG. 2).

Example 2

This example provides a description of the synthesis of a PCPP using soluble modifying agents.

PCPP was synthesized as described in U.S. Pat. No. 5,760,271. Briefly, instead of using solid dispersion as in Example 1, the modifying agent, NaPP, was dissolved in the reaction mixture using a solution of molten propyl paraben PP in diglyme (NaPP/PP=1.13 (w/w)), which was then used for the substitution of poly(dichlorophosphazene). PCPP was then produced by following a common reaction scheme-hydrolysis of substituted derivative with potassium chloride and purification by precipitating in aqueous sodium chloride and ethanol.

Example 3

This example provides a description of comparison of molecular weights of examples of PCPP-HM and PCPP.

The molecular weights of PCPP-HM (Example 1) and PCPP (Example 2) were determined by size-exclusion high performance liquid chromatography (SE-HPLC). The analysis was performed using a Hitachi Elite LaChrom liquid chromatography system equipped with a Hitachi L-2455 diode array detector and Waters Ultrahydrogel linear column. Phosphate buffered saline (PBS) was employed as a mobile phase. Weight averaged molecular weight was calculated by comparison with poly(acrylic acid) molecular weight standards. The weight average molecular weight (Mw) of PCPP-HM (Example 1) was 850,000 g/mol, whereas Mw for PCPP (Example 2) was 600,000 g/mol.

Example 4

This example provides a description of comparison of molecular sizes of examples of PCPP-HM and PCPP.

Figure 3:
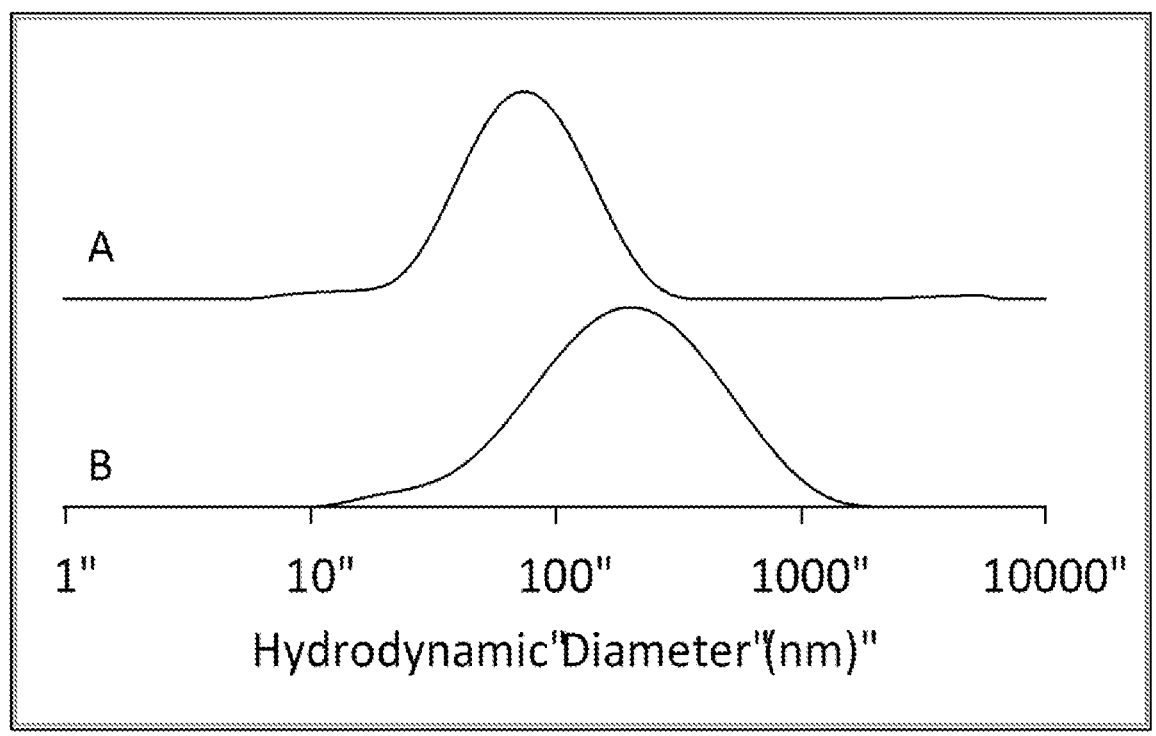
FIG. 3 shows the dynamic light scattering profiles of (A) PCPP and (B) PCPP-HM (polymer concentration—0.5 mg/mL, PBS).

The molecular sizes of PCPP-HM (Example 1) and PCPP (Example 2) were determined by Dynamic light scattering (DLS) using a Malvern Nano-ZS Zetasizer. Each sample was analyzed in PBS at a polymer concentration of 0.5 mg/mL. FIG. 3 shows size distribution profiles for PCPP (A) and PCPP-HM (B) revealing larger molecular size of PCPP-HM. This is confirmed by the values of peak average hydrodynamic diameter of PCPP-HM and PCPP—260 nm and 84 nm correspondingly or z-average hydrodynamic diameter of PCPP-HM and PCPP—138 nm and 60 nm correspondingly.

Example 5

This example provides a description of the stability of polyphosphazene adjuvant, PCPP in the presence of various sodium salts.

Figure 4:
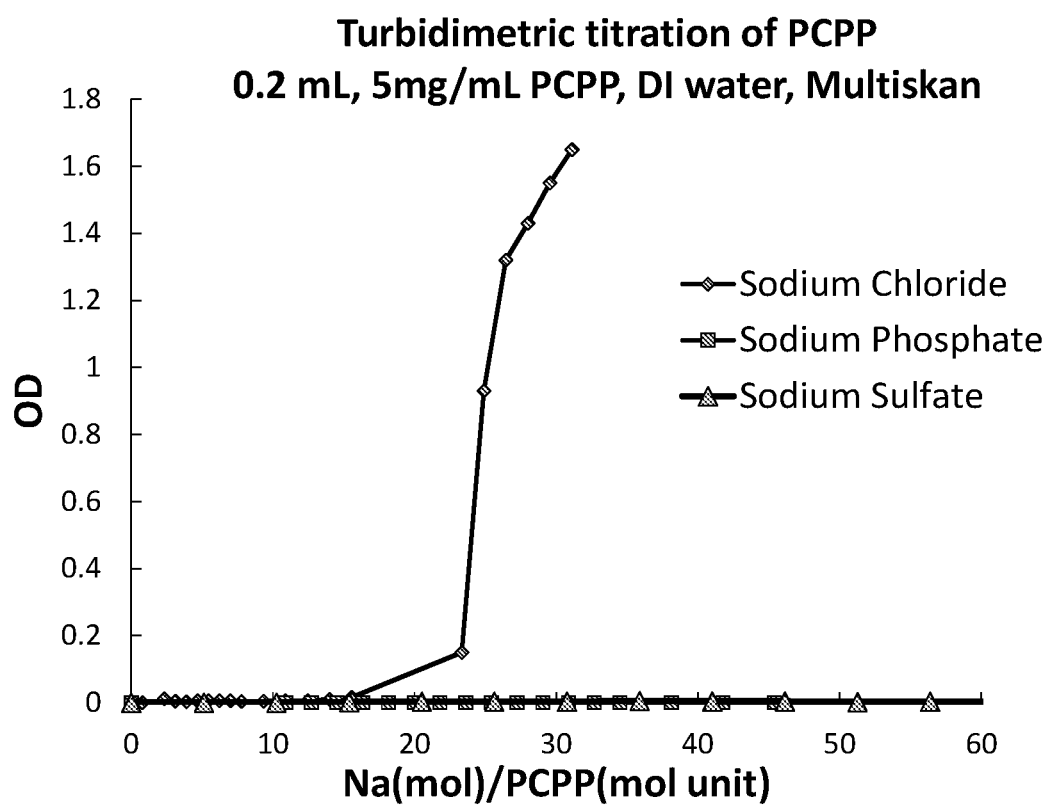
FIG. 4 shows the turbidimetric titration of PCPP. The results are presented as a dependence of the optical density of the solution or suspension on the concentration of salt.

Solutions of PCPP (0.5% w/v), sodium chloride (10% w/v), sodium phosphate (mixture of sodium phosphate dibasic (11.5% w/v), sodium phosphate monobasic (1.45% w/v), pH 7.4), and 10% of sodium sulfate were prepared by dissolving solid powder in deionized water. All solutions were filtered using 0.45 μm Millex filters (EMD Millipore, Billerica, Mass.) prior to titration. Turbidimetric titration was performed at an ambient temperature by measuring the absorbance of the mixture at 420 nm (Multiscan Spectrum, Fisher Corporation). Solution of PCPP (0.2 mL) was placed in 96 wells, shaken for 15 seconds after addition of the titrant and monitored in the spectrophotometer until a stable turbidity reading (±0.1% T) was obtained. The results are presented as a dependence of the optical density of the solution or suspension on the concentration of salt (FIG. 4). The increase in optical density for the system containing PCPP and sodium chloride clearly indicates phase separation in this system. It is also evident that the solutions remain homogeneous in case of titration of PCPP with sodium sulfate or sodium phosphates. Therefore it can be concluded that although sodium chloride causes phase separation of PCPP, sodium ions in the absence of chloride fail to cause any aggregation or phase separation of PCPP.

The invention claimed is:

1. A polyphosphazene product having the following structure:

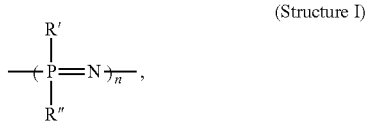
(Structure I)

a salt thereof, or a crosslinked analog thereof, wherein R' and R" are a combination of carboxylatophenoxy groups and trifluoroethoxy groups;
wherein n is an integer from 10 to 500,000, and
the polyphosphazene product has less than 2% by weight chloride, wherein the polyphosphazene product when placed in an aqueous solution results in no detectable aggregates.

2. The polyphosphazene product of claim 1, wherein the polyphosphazene product is a salt and the cation is selected from ammonium, potassium, sodium, calcium, iron, magnesium, quaternary ammonium, spermine, spermidine, and combinations thereof.

3. The polyphosphazene product of claim 1, wherein the polyphosphazene product is crosslinked covalently or non-covalently.

4. A composition comprising one or more polyphosphazene product of claim 1.

5. The composition of claim 4, wherein the composition further comprises a pharmaceutically acceptable carrier.

6. The composition of claim 4, wherein the composition further comprises one or more salts, wherein the one or more salts do not comprise a chloride ion.

7. The composition of claim 4, wherein at least one of the one or more polyphosphazenes product are crosslinked covalently or non-covalently.

8. The composition of claim 4, wherein the composition further comprises an immunologically active compound and the immunologically active compound is encapsulated by the crosslinked polyphosphazene product.

9. A method of making the polyphosphazene product of claim 1 comprising:
a) providing a reaction mixture comprising a polyphosphazene having the following structure:

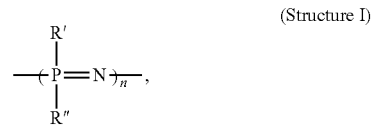
(Structure I)

a salt thereof, or a crosslinked analog thereof, wherein R' and R" are a combination of carboxylatophenoxy groups and trifluoroethoxy groups,
b) adjusting the pH of the reaction mixture with a chloride-free acid such that a precipitate comprising the polyphosphazene product is formed; and
c) separating the precipitate from the reaction mixture to provide a polyphosphazene product of claim 1.

10. The method of claim 9, wherein the pH of the reaction mixture does not go below 3.0, but does not exceed 6.5.

11. The method of claim 9, wherein the pH of the reaction mixture is adjusted by adding an acid salt comprising monovalent cations to the reaction mixture.

12. The method of claim 11, wherein the acid salt is selected from the group potassium hydrogen phthalate, disodium hydrogen phthalate, dipotassium hydrogen phthalate, sodium citrate, sodium acetate, sodium dihydrogen orthophospate, potassium dihydrogen orthophosphate, or disodium hydrogen orthophosphate.

13. The method of claim 9, wherein the pH of the reaction mixture is adjusted by addition of carbon dioxide to the reaction mixture.

* * * * *